(12) United States Patent
Park et al.

(10) Patent No.: US 11,076,830 B2
(45) Date of Patent: Aug. 3, 2021

(54) ULTRASOUND IMAGING APPARATUS AND METHOD OF CONTROLLING THE SAME

(71) Applicant: SAMSUNG ELECTRONICS CO., LTD., Suwon-si (KR)

(72) Inventors: Su Hyun Park, Hwaseong-si (KR); Kyu Hong Kim, Seoul (KR); Bae Hyeong Kim, Yongin-si (KR); Jung Ho Kim, Yongin-si (KR); Joo Young Kang, Yongin-si (KR); Young Ihn Kho, Seoul (KR); Yun-Tae Kim, Suwon-si (KR); Sung Chan Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 672 days.

(21) Appl. No.: 14/843,309

(22) Filed: Sep. 2, 2015

(65) Prior Publication Data

US 2016/0058419 A1   Mar. 3, 2016

(30) Foreign Application Priority Data

Sep. 2, 2014 (KR) .................. 10-2014-0116248
Jul. 27, 2015 (KR) .................. 10-2015-0105777

(51) Int. Cl.
    *A61B 8/08*      (2006.01)
    *A61B 8/00*      (2006.01)
    *G01S 7/52*      (2006.01)
    *B06B 1/02*      (2006.01)

(52) U.S. Cl.
    CPC ............. *A61B 8/481* (2013.01); *A61B 8/464* (2013.01); *A61B 8/54* (2013.01); *B06B 1/0215* (2013.01); *G01S 7/52039* (2013.01); *G01S 7/52041* (2013.01); *B06B 2201/76* (2013.01)

(58) Field of Classification Search
    CPC .................................................. A61B 8/0481
    See application file for complete search history.

(56) References Cited

U.S. PATENT DOCUMENTS

| 2002/0022780 A1* | 2/2002 | Kawagishi | ........... A61B 8/4281 600/443 |
| 2005/0245828 A1* | 11/2005 | Tsujino | .................... A61B 8/06 600/453 |
| 2008/0200815 A1* | 8/2008 | Van Der Steen | ........ A61B 8/12 600/467 |

(Continued)

OTHER PUBLICATIONS

Dijkmans et al, Microbubbles and ultrasoundL from diagnosis to therapy, 2004, Elsevier, 5, 245-256 (Year: 2004).*

*Primary Examiner* — Rochelle D Turchen
(74) *Attorney, Agent, or Firm* — Sughrue Mion, PLLC

(57) ABSTRACT

An ultrasound imaging apparatus and a method of controlling the same are provided. The ultrasound imaging apparatus includes an ultrasound contrast agent (UCA) sensor configured to determine whether an UCA flows in an object based on an echo signal that is reflected by the object in a mechanical index environment. The ultrasound imaging apparatus further includes a controller configured to obtain at least one among an UCA image and a tissue image of the object in another mechanical index environment lower than the mechanical index environment in response to the UCA sensor determining that the UCA flows in the object.

8 Claims, 15 Drawing Sheets

(56) References Cited

U.S. PATENT DOCUMENTS

| | | | |
|---|---|---|---|
| 2009/0227872 A1* | 9/2009 | Pan | A61B 8/481 |
| | | | 600/458 |
| 2012/0027282 A1* | 2/2012 | Yoshikawa | A61B 8/06 |
| | | | 382/131 |
| 2012/0184849 A1* | 7/2012 | Sandstrom | A61B 8/48 |
| | | | 600/438 |

* cited by examiner

ULTRASOUND IMAGING APPARATUS AND METHOD OF CONTROLLING THE SAME

CROSS-REFERENCE TO RELATED APPLICATIONS

This application claims priority from Korean Patent Application No. 10-2014-0116248, filed on Sep. 2, 2014, and Korean Patent Application No. 10-2015-0105777, filed on Jul. 27, 2015, in the Korean Intellectual Property Office, the disclosures of which are incorporated herein in their entireties by reference.

BACKGROUND

1. Field

Apparatuses and methods consistent with exemplary embodiments relate to an ultrasound imaging apparatus and a method of controlling the same.

2. Description of the Related Art

Ultrasound imaging apparatuses each transmit an ultrasound signal generated by a transducer of a probe to an object and receive the information of an echo signal reflected by the object, thereby obtaining an image of a portion inside the object. Particularly, ultrasound imaging apparatuses are used for medical purposes such as observing the inside of the object, detecting foreign substances, and measuring injuries. Because ultrasound imaging apparatuses have high stability, are able to display images in real time, and are safe without irradiation exposure compared with diagnostic apparatuses using X-rays, the ultrasound imaging apparatuses are used together with other image diagnostic apparatuses.

Meanwhile, ultrasound contrast agents (UCAs) are used with ultrasound imaging apparatuses. UCAs are injected into objects to improve a contrast between tissues, thereby providing more precise ultrasound images.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments include an ultrasound imaging apparatus that controls a mechanical index according to an inflow of an ultrasound contrast agent (UCA) and a method of controlling the same.

According to an aspect of an exemplary embodiment, an ultrasound imaging apparatus includes an ultrasound contrast agent (UCA) sensor configured to determine whether an UCA flows in an object based on an echo signal that is reflected by the object in a mechanical index environment, and a controller configured to obtain at least one among an UCA image and a tissue image of the object in another mechanical index environment lower than the mechanical index environment in response to the UCA sensor determining that the UCA flows in the object.

The UCA sensor may be further configured to detect a harmonic frequency signal from the echo signal, and determine that the UCA flows in the object in response to the UCA sensor detecting the harmonic frequency signal.

The controller may be further configured to obtain the UCA image based on the harmonic frequency signal that is reflected by the UCA, and obtain the tissue image based on a fundamental frequency signal that is reflected by tissue of the object.

The other mechanical index environment may include a first mechanical index environment or a second mechanical index environment, and the mechanical index environment may include the third mechanical index environment.

The third mechanical index environment may be a mechanical index range in which the UCA collapses, the second mechanical index environment may be a mechanical index range in which the UCA nonlinearly moves, and the first mechanical index environment may be a mechanical index range in which the UCA linearly moves.

The controller may be further configured to obtain the tissue image in the first mechanical index environment, and obtain the UCA image in the second mechanical index environment.

The controller may be further configured to obtain the UCA image in the second mechanical index environment for a first time period, and obtain the tissue image in the first mechanical index environment for a second time period.

The controller may be further configured to obtain the UCA image by controlling a transmitting cycle of ultrasound in the second mechanical index environment to allow the UCA to collapse.

The ultrasound imaging apparatus may further include a display configured to display the tissue image and the UCA image.

The display may be further configured to alternately display the tissue image and the UCA image.

The display may be further configured to display a mechanical index that is used by the ultrasound imaging apparatus.

The UCA image may be generated in a first frequency band, and the tissue image may be generated in a second frequency band narrower than the first frequency band.

The UCA image may be generated by transmitting ultrasound according to a pulse inversion method.

According to an aspect of another exemplary embodiment, there is provided a method of controlling an ultrasound imaging apparatus, the method including determining whether an UCA flows in an object based on an echo signal that is reflected by the object in a mechanical index environment, and obtaining at least one among an UCA image and a tissue image of the object in another mechanical index environment lower than the mechanical index environment in response to the determining that the UCA flows in the object.

The determining may include detecting a harmonic frequency signal from the echo signal, and determining that the UCA flows in the object in response to the detecting the harmonic frequency signal.

The other mechanical index environment may include a first mechanical index environment being a mechanical index range in which the UCA linearly moves, or a second mechanical index environment being a mechanical index range in which the UCA nonlinearly moves, and the mechanical index environment may include a third mechanical index environment being a mechanical index range in which the UCA collapses.

The obtaining may include obtaining the UCA image by controlling a transmitting cycle of ultrasound in the second mechanical index environment to allow the UCA to collapse.

The obtaining may include obtaining the tissue image by transmitting ultrasound in the first mechanical index environment to the object.

The obtaining may include obtaining the UCA image by transmitting ultrasound in the second mechanical index environment to the object.

According to an aspect of another exemplary embodiment, an ultrasound imaging apparatus includes an ultrasound contrast agent (UCA) sensor configured to determine whether an UCA flows in an object based on a harmonic frequency signal that is reflected by the UCA in a third mechanical index environment in which the UCA destructs, and a controller configured to obtain an UCA image of the object based on a harmonic frequency signal that is reflected by the UCA in a second mechanical index environment in which the UCA nonlinearly moves, and obtain a tissue image of the object based on a fundamental frequency signal that is reflected by the object in a first mechanical index environment in which the UCA linearly moves, in response to the UCA sensor determining that the UCA flows in the object.

BRIEF DESCRIPTION OF THE DRAWINGS

The above and/or other aspects will become more apparent by describing exemplary embodiments with reference to the accompanying drawings, in which.

DETAILED DESCRIPTION

Figure 1:
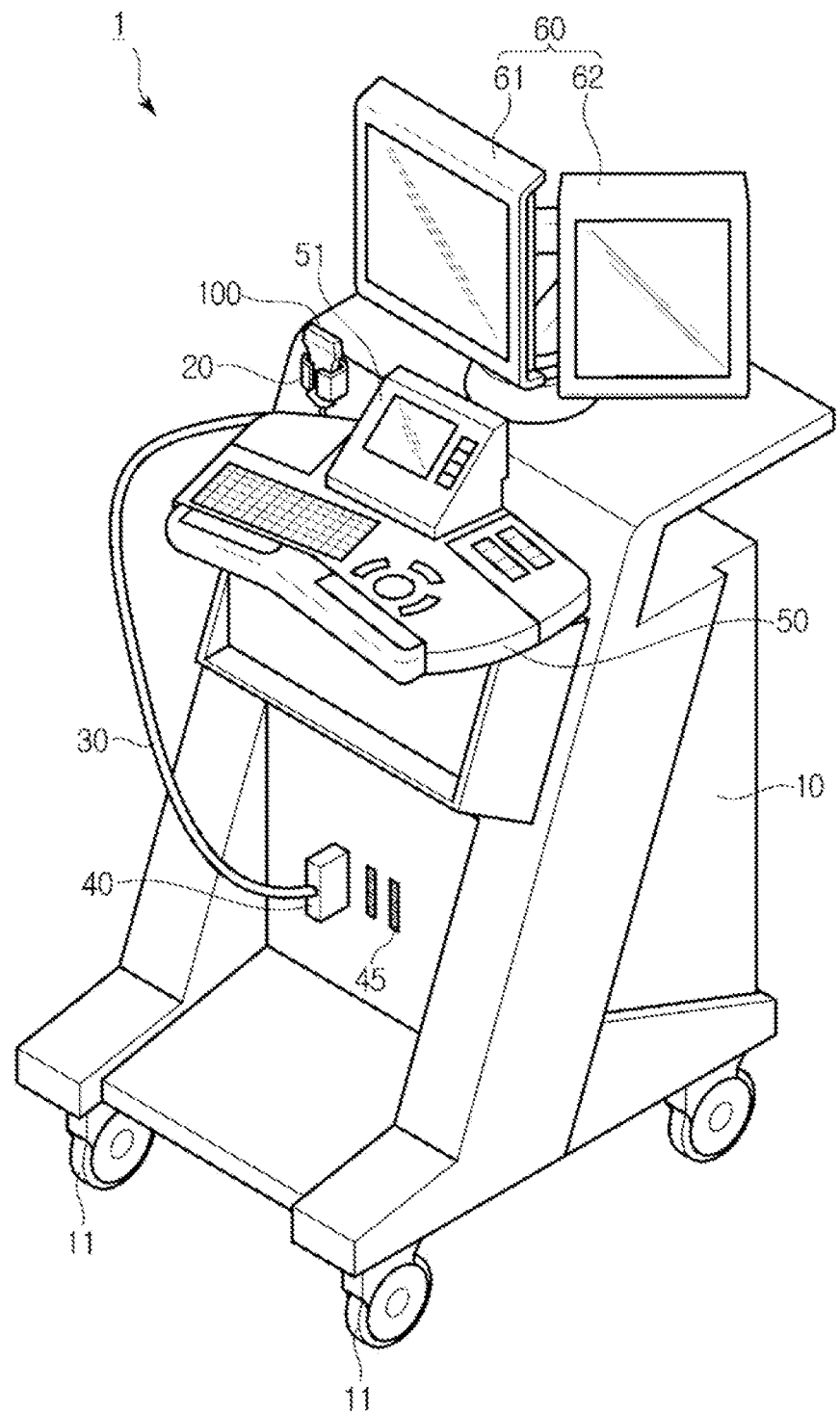
FIG. 1 is a perspective view of an ultrasound imaging apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions may not be described in detail because they would obscure the description with unnecessary detail.

Also, throughout the specification, "an object" may include a human, an animal or a part of the human or animal. For example, the object may include not only organs such as a liver, a heart, a womb, a brain, breasts, abdomen, or blood vessels, but also an embryo or fetus of a mother.

Also, throughout the specification, "a user" may be a medical expert such as a doctor, a nurse, a clinical pathologist, a medical imaging technician, etc., or may be a medical apparatus service engineer, but is not limited thereto.

Also, herein, "a mechanical index" is an index that quantifies an effect of mechanical effects of ultrasound on an object, in which as the mechanical index is higher, an effect on a human body is greater. The mechanical effect of the ultrasound is provided by a cavitation phenomenon, which occurs at a peak negative acoustic pressure of the ultrasound. Accordingly, the mechanical index may be defined by an acoustic working frequency and a level of the peak negative acoustic pressure, which is an absolute value.

Also, herein, "an ultrasound image" is an image of an object obtained using ultrasound. Here, "the ultrasound image" may be a two-dimensional or a three-dimensional image.

In detail, the ultrasound image may include a tissue image, which shows an anatomical structure of a target area of an object, and an ultrasound contrast agent (UCA) image, which shows an UCA of a target area.

The UCA strengthens a weak echo signal of an area in which it is difficult to obtain an ultrasound image thereof, for example, small veins, a blood vessel present deep inside an object, and a small lesion. The UCA is injected through a blood vessel of the object and moves inside the object while passing through the blood vessel. When the object is scanned with ultrasound, the UCA nonlinearly moves or backscatters while collapsing. An ultrasound imaging apparatus may generate an UCA image using the backscatter described above.

In detail, the UCA may include a microparticle contrast agent and a nanoparticle contrast agent.

For example, the microparticle contrast agent may be microbubbles. The microbubbles may have a size from about 1 to 4 μm. The microbubbles may be formed of a phospholipid membrane surrounding a gas such as perfluorocarbon (PFC).

Also, the nanoparticle contrast agent may be PFC nanodroplets or polylactic acid (PLA) nanobubbles. The PFC nanodroplets may have a size from about 200 to about 400 nm, and the PLA nanobubbles may have a size from about 40 to about 200 nm.

FIG. 1 is a perspective view of an ultrasound imaging apparatus 1 according to an exemplary embodiment. As shown in FIG. 1, the ultrasound imaging apparatus 1 includes an ultrasound probe 100, a body 10, an operation panel 50, and a display 60.

In front of a bottom of the body 10, one or more female connectors 45 are provided. Each of the female connectors 45 may be physically coupled with a male connector 40 provided at one end of a cable 30. Through the cable 30, the ultrasound probe 100 and the body 10 are connected.

Meanwhile, below the body 10, a plurality of castors 11 for providing mobility of the ultrasound imaging apparatus 1 are provided. A user may fix or move the ultrasound imaging apparatus 1 to a place or in a direction using the plurality of castors 11. The ultrasound imaging apparatus 1 described above is referred to as a cart type ultrasound imaging apparatus.

Meanwhile, unlike FIG. 1, the ultrasound imaging apparatus 1 may be a portable ultrasound imaging apparatus capable of being carried when moving long distances. Here, the portable ultrasound imaging apparatus may not include the castors 11. For example, the portable ultrasound imaging apparatus may include a picture archiving and communication system (PACS) viewer, a smart phone, a laptop computer, a personal digital assistant (PDA), a tablet personal computer (PC), etc. but is not limited thereto.

The ultrasound probe 100 is a portion in contact with a body surface of an object, and may transmit and receive ultrasound to and from the object. In detail, the ultrasound probe 100 generates and transmits ultrasound according to an input pulse into the object, and receives echo ultrasound reflected by a part inside the object. The ultrasound probe 100 will be described below in detail.

The operation panel 50 receives a command related to an operation of the ultrasound imaging apparatus 1. The user may input commands to perform the start of a diagnosis, a selection of a diagnosis area, a selection of a diagnosis type, a selection of a mode for an ultrasound image finally output, etc. For example, the mode for the ultrasound image may include an amplitude mode (A-mode), a brightness mode (B-mode), a Doppler mode (D-mode), an elastography mode (E-mode), a motion mode (M-mode), etc.

As an exemplary embodiment, the operation panel 50, as shown in FIG. 1, is located above the body 10. Here, the operation panel 50 may include at least one of a switch, a key, a wheel, a joystick, a trackball, and a knob.

Also, the operation panel 50 further includes a sub display 51. The sub display 51 may be provided at one side of the operation panel 50, and displays information related to the operation of the ultrasound imaging apparatus 1.

For example, the sub display 51 may display a menu or guidance notice for setting the ultrasound imaging apparatus 1 or display present settings of the ultrasound imaging apparatus 1.

Here, the sub display 51 may be formed of a touch panel. When the sub display 51 is formed of the touch panel, the user may input a control command by touching the sub display 51.

The sub display 51, for example, may be formed of one of a liquid crystal display (LCD) panel, a light emitting display (LED) panel, and an organic LED (OLED) panel.

The display 60 may display ultrasound images obtained during an ultrasound diagnosis process. The display 60, as shown in FIG. 1, is coupled with and mounted on the body 10, but may be formed separately from the body 10.

Around the operation panel 50, at least one probe holder 20 for holding the ultrasound probe 100 is provided. Accordingly, when the ultrasound imaging apparatus 1 is not used, the user may store the ultrasound probe 100 on the probe holder 20.

Also, the display 60 includes a plurality of displays 61 and 62 to display different types of images at the same time. For example, a first display 61 may display a two-dimensional ultrasound image, and a second display 62 may display a three-dimensional ultrasound image. Also, the first display 61 may display a diagnosis image, and the second display 62 may display an UCA image.

Also, the respective displays 61 and 62 may employ displays such as a plasma display panel (PDP), an LCD panel, an LED panel, an OLED panel, an active-matrix OLED (AMOLED) panel, etc.

Figure 2:
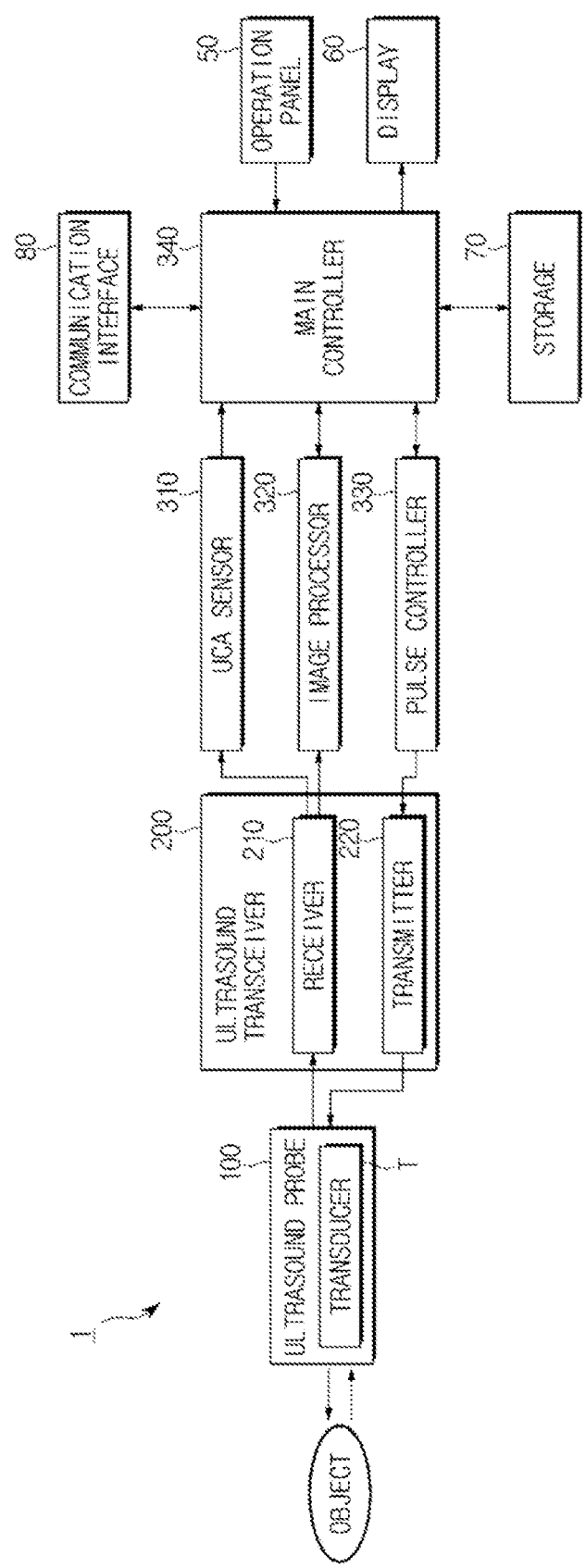
FIG. 2 is a control block diagram of the ultrasound imaging apparatus of FIG. 1.

FIG. 2 is a control block diagram of the ultrasound imaging apparatus 1 of FIG. 1.

As shown in FIG. 2, the ultrasound imaging apparatus 1 includes a communication interface 80, a storage 70, the ultrasound probe 100, an ultrasound transceiver 200, an UCA sensor 310, an image processor 320, a pulse controller 330, and a main controller 340.

The communication interface 80 may be connected to another apparatus, and may transmit and receive data with the connected apparatus. For example, the communication interface 80 may send and receive data with a clinic server or other medical apparatuses in a clinic connected through a PACS.

Also, the communication interface 80 may communicate data with other apparatuses according to various wired/wireless communication protocols and according to digital imaging and communications in medicine (DICOM) standards.

In detail, the communication interface 80 may be connected to another apparatus to receive previously taken ultrasound images, computed tomography images, and magnetic resonance (MR) images from the outside, or to transmit ultrasound images obtained from an object to the other apparatus. Also, the communication interface 80 may receive information related to a diagnosis history, a treatment schedule, etc. of a patient stored in the server. Also, the communication interface 80 may perform data communication with a portable device such as a smart phone.

The storage 70 may store various types of information for driving the ultrasound imaging apparatus 1. For example, the storage 70 may store medical data related to diagnosing the object such as an echo signal and an ultrasound image, and may store a program for driving the ultrasound imaging apparatus 1.

Also, the storage 70, for example, may include a high-speed random access memory (RAM), a magnetic disc, a static RAM (SRAM), a dynamic RAM (DRAM), and a read-only memory (ROM), but is not limited thereto.

Also, the storage 70 may be detachable from the ultrasound imaging apparatus 1. For example, the storage 70 may include a compact flash (CF) card, a secure digital (SD) card, a smart media (SM) card, a multimedia card (MMC), and a memory stick, but is not limited thereto. Also, the storage 70 may be provided outside the ultrasound imaging apparatus 1, and may transmit and receive data to and from the ultrasound imaging apparatus 1 through wired and wireless communication.

The ultrasound probe 100 transmits ultrasound to the object, and receives an echo signal reflected therefrom while being in contact with a surface of the object. Hereinafter, referring to FIGS. 2 to 4, the ultrasound probe 100 and transmission and receiving of ultrasound will be described in detail.

Figure 3:
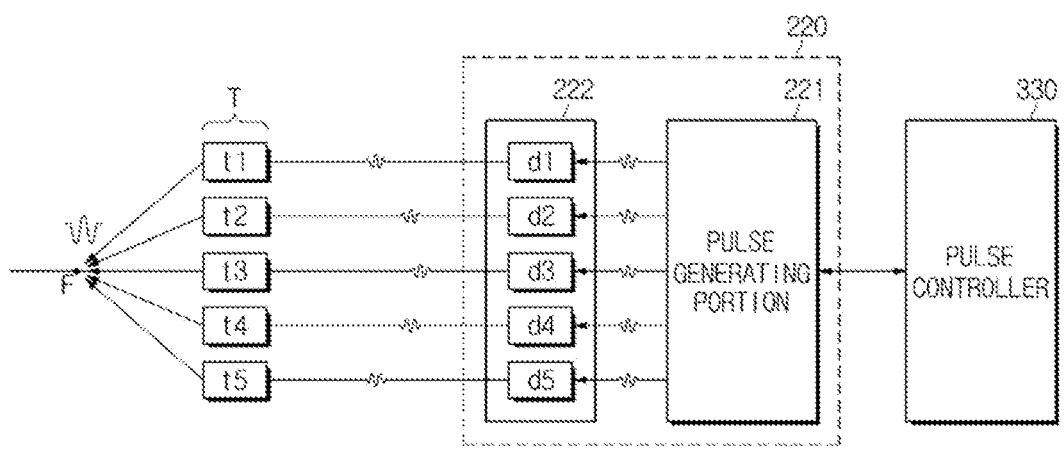
FIG. 3 is a control block diagram illustrating a process of transmitting ultrasound, according to an exemplary embodiment.
Figure 4:
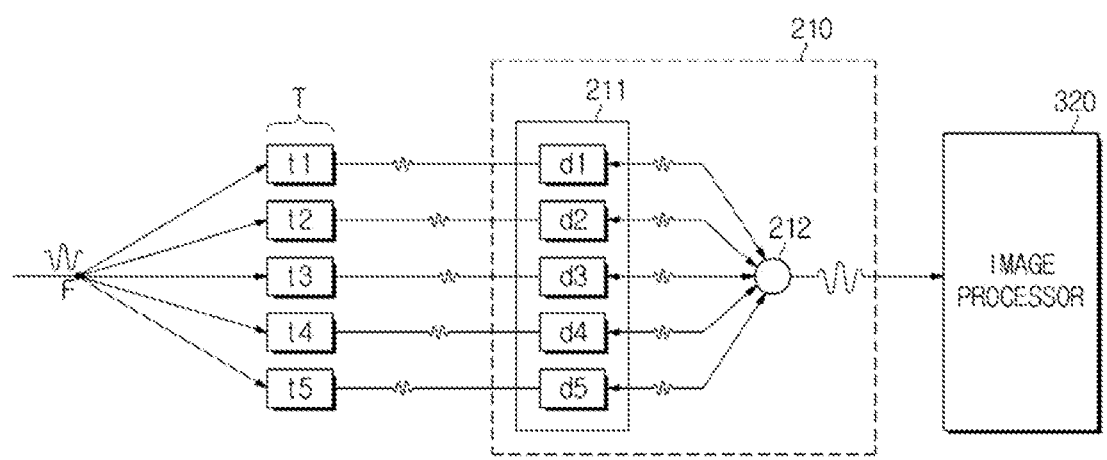
FIG. 4 is a control block diagram illustrating a process of receiving ultrasound, according to an exemplary embodiment.

FIG. 3 is a control block diagram illustrating a process of transmitting ultrasound, according to an exemplary embodiment. FIG. 4 is a control block diagram illustrating a process of receiving ultrasound, according to an exemplary embodiment.

As shown in FIGS. 2 to 4, the ultrasound probe 100 includes a transducer T. Here, the transducer T indicates a device that converts energy in a form into energy in another form. For example, the transducer T may convert electric energy into wave energy, and may convert wave energy into electric energy.

In detail, the transducer T may include a piezoelectric material or a piezoelectric thin film. When an alternating current is applied to the piezoelectric material or the piezoelectric thin film from an internal capacitor such as a battery or an external power supply device, the piezoelectric material or the piezoelectric thin film oscillates at a frequency, and ultrasound at the frequency is generated according to oscillation frequency.

On the contrary, when an ultrasound echoed at a frequency arrives at the piezoelectric material or the piezoelectric thin film, the piezoelectric material or the piezoelectric thin film is allowed to oscillate according to the frequency of the echoed ultrasound which arrives. Here, the piezoelectric material or the piezoelectric thin film outputs an alternating current at a frequency corresponding to the oscillation frequency.

Also, as the transducer T, various types of transducers such as a magnetostrictive ultrasonic transducer using a magnetostrictive effect of a magnetic material, a piezoelectric ultrasonic transducer using a piezoelectric effect of a piezoelectric material, a capacitive micromachined ultrasonic transducer (CMUT) that transmits and receives ultrasound using the oscillation of several tens or thousands of micromachined thin films, etc. may be used. Additionally, different types of devices capable of generating ultrasound according to an electric signal or generating an electric signal according to ultrasound may be also used as the transducer T.

The ultrasound transceiver 200 applies a driving signal to the ultrasound probe 100, and focuses an echo signal received from the ultrasound probe 100. That is, the ultrasound transceiver 200 may perform beamforming. In detail, the ultrasound transceiver 200 includes a receiver 210 and a transmitter 220.

The transmitter 220 performs transmission beamforming. As shown in FIG. 3, distances between a plurality of transducers t1 to t5 and a focus F differ from one another. Accordingly, the transmitter 220 may perform beamforming to focus ultrasound transmitted to the focus F.

In detail, the transmitter 220 includes a pulse generating portion 221 and a first delay portion 222.

The pulse generating portion 221 generates a pulse according to a control signal of the pulse controller 330. Here, the pulse controller 330 outputs a control signal to the pulse generating portion 221 to generate an ultrasound signal corresponding to a mechanical index determined by the main controller 340.

Meanwhile, the pulse generated by the pulse generating portion 221 may be a pulse having a pulse repetition frequency (PRF).

The first delay portion 222 delays respective pulses output by the pulse generating portion 221 for times, and then outputs. The first delay portion 222 includes a plurality of delayers d1 to d5. Here, the plurality of delayers d1 to d5 is connected with the transducers t1 to t5, respectively. In detail, as shown in FIG. 3, the pulses generated by the pulse generating portion 221 are input to the delayers d1 to d5, respectively.

The delayers d1 to d5 delay the input pulses for times, and then output. Here, the delay times of the respective delayers d1 to d5 are determined according to the distances between the respective transducers t1 to t5 and the focus F. That is, the second delayer d2 to the fourth delayer d4 delay the input pulses for times and then output to allow ultrasound signals transmitted from the second transducer t2 to the fourth transducer t4 to arrive at the focus F when ultrasound signals transmitted from the first transducer t1 and the fifth transducer t5, whose distances from the focus F are long, arrive at the focus F.

As described above, ultrasound transmitted through the transducer T is reflected by an object and is incident upon the transducer T. When an ultrasound echoed by the object is received like this, the respective transducers t1 to t5 outputs echo signals corresponding to the received ultrasound. The echo signals output as described are focused by the receiver 210. Referring to FIG. 4, the receiver 210 includes a second delay portion 211 and a synthesizing portion 212.

The second delay portion 211 outputs an input echo signal for a time. The second delay portion 211 includes a plurality of delayers d1 to d5. Here, the plurality of delayers d1 to d5 is connected with the transducers t1 to t5, respectively.

Here, because distances between the focus F and the respective transducers t1 to t5 differ from one another, points in time when the echo ultrasound arrives at the respective transducers t1 to t5 mutually differ. Accordingly, to focus the echo signals, the echo signals input to the respective delayers d1 to d5 are delayed for times and then output.

For example, the third delayer d3 to which the echo signal is input first delays the input echo signal until the echo signals are input to the first delayer d1 and the fifth delayer d5 and then output.

The synthesizing portion 212 synthesizes the echo signals output from the respective delayers d1 to d5. Here, the synthesizing portion 212 may focus the plurality of echo signals, but may synthesize the respective echo signals by applying weights thereto. Here, the weights may be determined regardless of the echo signals, but may be determined based on the echo signals.

The image processor 320 generates an ultrasound image based on the echo signals output from the receiver 210. For example, the image processor 320 may generate at least one of an A-mode image, a B-mode image, a D-mode image, an E-mode image, and an M-mode image based on the echo signals. In addition, the image processor 320 may generate a three-dimensional ultrasound image based on a plurality of ultrasound images obtained from the echo signals. A method of processing an ultrasound image will be described below in detail.

Here, the image processor 320 may correspond to one or more processors. Here, the processors may be provided as a plurality of logic gate arrays, or may be provided as a combination of a microprocessor and a memory in which a program executable in the microprocessor is stored. For example, the image processor 320 may be provided as a graphic processor (GPU).

Referring to FIG. 2 again, the UCA sensor 310 senses an inflow of an UCA. Due to properties of the UCA, to effectively generate an UCA image, a mechanical index may be appropriately adjusted. Hereinafter, a correlation between the mechanical index and the UCA will be described in detail.

Figure 5:
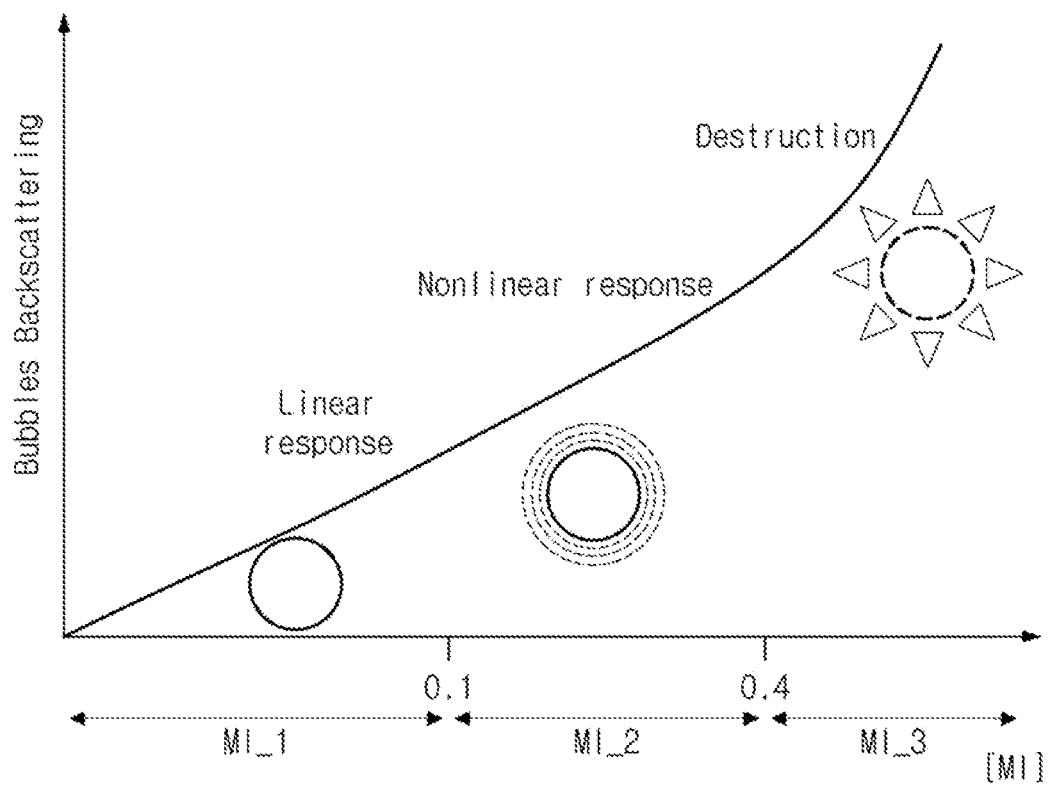
FIG. 5 is a graph illustrating a correlation between a mechanical index and an ultrasound contrast agent (UCA), according to an exemplary embodiment.

FIG. 5 is a graph illustrating a correlation between a mechanical index and an UCA, according to an exemplary embodiment.

Depending on a mechanical index of ultrasound output from the ultrasound probe 100, a state of the UCA (e.g., bubbles backscattering) varies. A mechanical index environment may be defined according to a level of the mechanical index. The mechanical index environment indicates the level of the mechanical index. As shown in FIG. 5, a first mechanical index environment MI_1 may be defined as a mechanical index section in which a linear movement or response of the UCA is shown, a second mechanical index environment MI_2 may be defined as a mechanical index section in which a nonlinear movement of the UCA is shown, and a third mechanical index environment MI_3 may be defined as a mechanical index section in which the UCA collapses or destructs. Also, a random mechanical index included in the first mechanical index environment may be defined as a first mechanical index, a random mechanical index included in the second mechanical index environment may be defined as a second mechanical index, and a random mechanical index included in the third mechanical index environment may be defined as a third mechanical index.

In detail, in the third mechanical index environment MI_3 in which a mechanical index is greater than 0.4, the UCA collapses and generates backscatter. In the second mechanical index environment MI_2 in which a mechanical index is smaller than 0.4 and greater than 0.1, the UCA nonlinearly moves and generates backscatter. Also, in the first mechanical index environment MI_1 in which a mechanical index is smaller than 0.1, the UCA linearly moves.

Meanwhile, according to oscillation properties of the UCA, ranges of the first mechanical index environment MI_1, the second mechanical index environment MI_2, and the third mechanical index environment MI_3 may vary.

An UCA image may be obtained by using backscatter which occurs due to the nonlinear movement or collapse of the UCA. However, in the third mechanical index environment MI_3 of obtaining a tissue image, because the UCA rapidly collapses, it may be difficult to obtain a proper UCA image.

In addition, when the UCA is injected into a blood vessel in the third mechanical index environment MI_3, the UCA rapidly collapses and a cavitation phenomenon occurs, thereby having a bad effect on an object.

Accordingly, it is determined whether an UCA flows into an ultrasound-scanned area, and whether to control a mechanical index environment depending on whether the UCA flows into or not. Hereinafter, a method of determining an inflow of an UCA will be described in detail with reference to FIG. 6.

Figure 6:
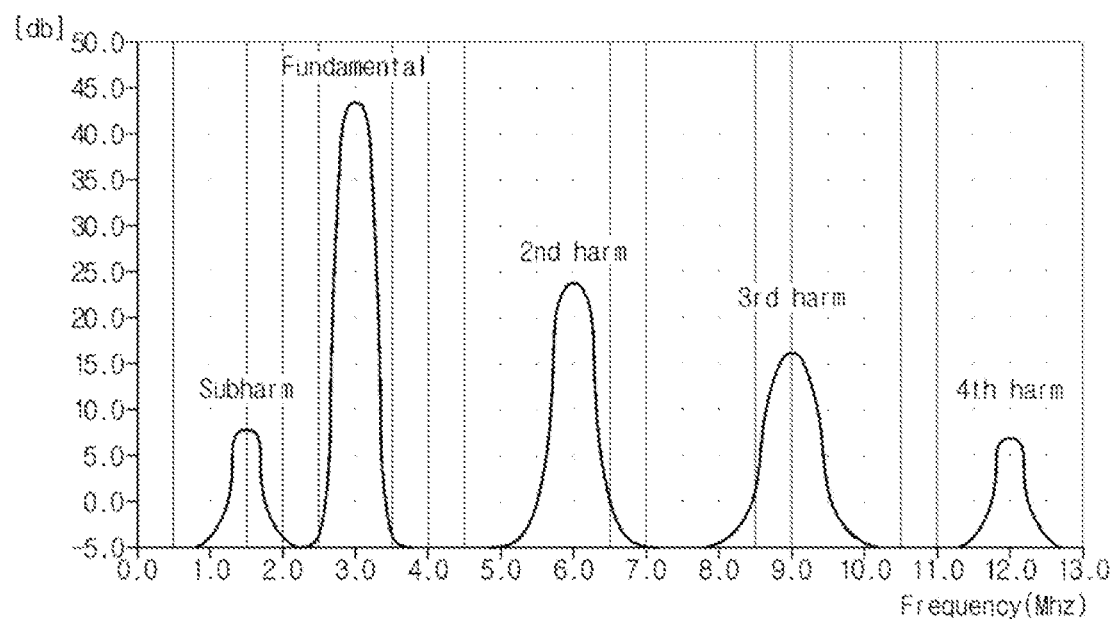
FIG. 6 is a graph illustrating a distribution of an echo signal in an environment in which an UCA is injected, according to an exemplary embodiment.

FIG. 6 is a graph illustrating a distribution of an echo signal in an environment in which an UCA flows, according to an exemplary embodiment. FIG. 6 illustrates an echo signal in a case in which ultrasound at 3.0 Mhz is transmitted. As shown in FIG. 6, the echo signal may include a fundamental frequency at 3.0 Mhz but also harmonic frequencies.

As described above, due to the backscatter of the UCA, the echo signals are observed not only at the fundamental frequency but also at the harmonic frequencies. In detail, the echo signal is observed at a second harmonic frequency at 6.0 Mhz twice the fundamental frequency, a third harmonic frequency at 9.0 Mhz three times the fundamental frequency, a fourth harmonic frequency at 12.0 Mhz four times the fundamental frequency, and a sub harmonic frequency at 1.5 Mhz half the fundamental frequency.

Accordingly, when harmonic frequencies are detected from an echo signal, referring again to FIG. 2, the UCA sensor 310 may determine that an UCA flows therein. In more detail, the UCA sensor 310 may determine that the UCA flows in when a peak of the harmonic frequency is detected, when a harmonic frequency signal changes more than a threshold, or when a harmonic frequency signal has a level of a reference or more.

For this, the UCA sensor 310 may monitor signals in overall frequency domains of the echo signal.

The main controller 340 controls the ultrasound imaging apparatus 1. In detail, the main controller 340 obtains an ultrasound image by appropriately controlling a mechanical index depending on whether the UCA flows in.

The main controller 340 may correspond to one or more processors. Here, the processors may be provided as a plurality of logic gate arrays, or may be provided as a combination of a microprocessor and a memory in which a program executable in the microprocessor is stored.

In FIG. 2, the main controller 340 and the UCA sensor 310 are separately provided. However, the main controller 340 and the UCA sensor 310 may be provided as a single processor. Also, the pulse controller 330 may be included in the main controller 340.

Also, the main controller 340 may directly receive an echo signal, and may generate an ultrasound image. It will be understood that the image processor 320 may be omitted when the main controller 340 generates the ultrasound image as described above.

The main controller 340 controls respective components to provide an optimal ultrasound image to the user by properly controlling a mechanical index when an UCA flows in. Hereinafter, a method of controlling the ultrasound imaging apparatus 1 according to an inflow of an UCA, according to exemplary embodiments will be described with reference to FIGS. 7 to 10.

Figure 7:
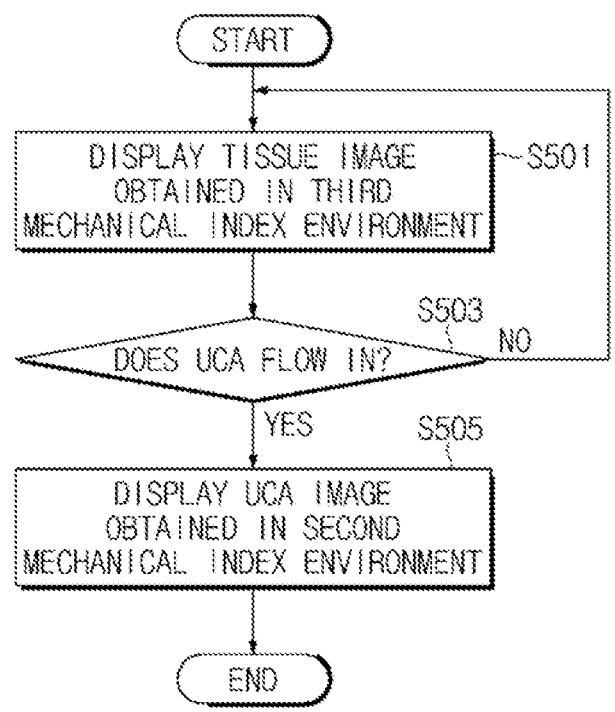
FIG. 7 is a flowchart illustrating a method of controlling an ultrasound imaging apparatus, according to an exemplary embodiment.
Figure 8:
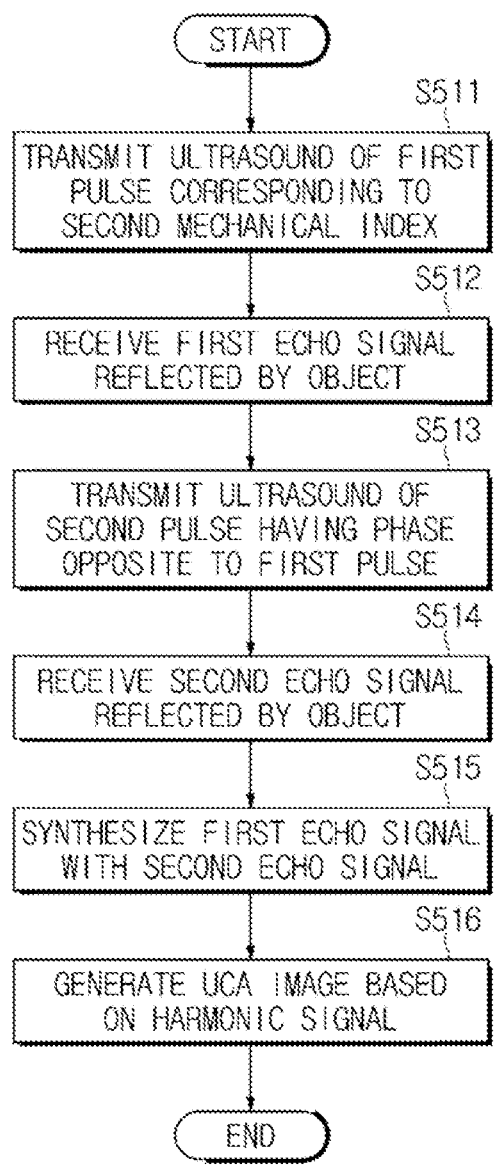
FIG. 8 is a flowchart illustrating a method of obtaining an UCA image, according to an exemplary embodiment.
Figure 9:
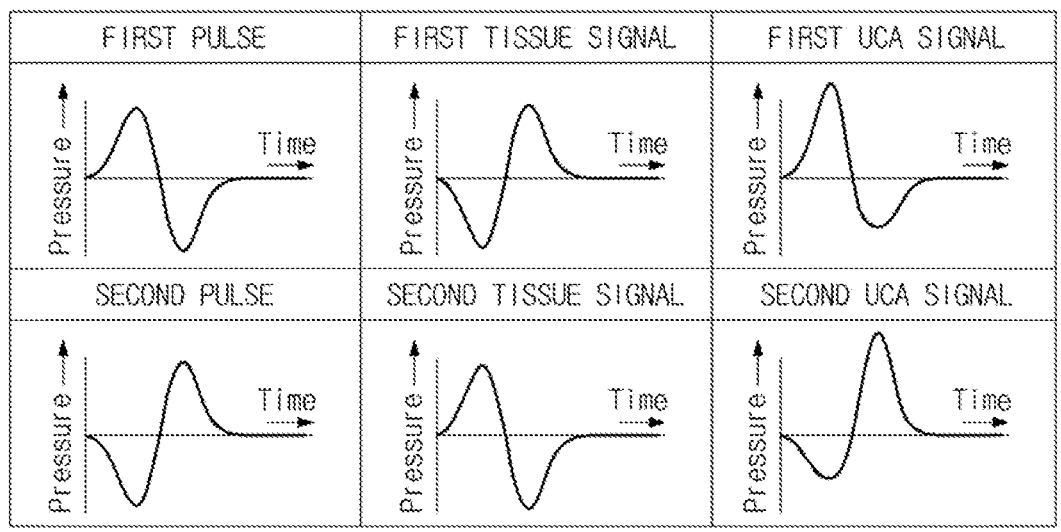
FIG. 9 is a view illustrating input pulses for obtaining an UCA image and echo signals according to the input pulses, according to an exemplary embodiment.
Figure 10:
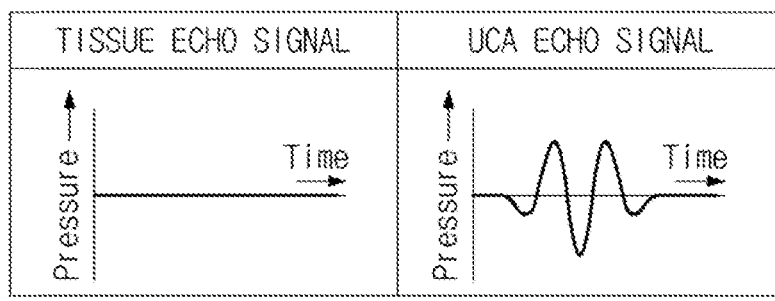
FIG. 10 is a view illustrating a sum of the echo signals shown in FIG. 9.

FIG. 7 is a flowchart illustrating a method of controlling the ultrasound imaging apparatus 1, according to an exemplary embodiment. FIG. 8 is a flowchart illustrating a method of obtaining an UCA image, according to an exemplary embodiment. FIG. 9 is a view illustrating input pulses for obtaining an UCA image and echo signals according to the input pulses, according to an exemplary embodiment. FIG. 10 is a view illustrating a sum of the echo signals shown in FIG. 9.

Referring to FIG. 7, in operation S501, the main controller 340 displays a tissue image obtained in the third mechanical index environment MI_3. In detail, the main controller 340 may control the pulse controller 330 to transmit an ultrasound signal of the third mechanical index, and may control the receiver 210 and the image processor 320 to focus echo signals, thereby obtaining the tissue image. The tissue image obtained as described above may be displayed through the display 60, and may be stored in the storage 70.

In operation S503, the UCA sensor 310 determines an inflow of an UCA or whether the UCA flows in the tissue image. When the UCA flows in (Yes for S503), the method continues in operation S505. Otherwise, the method returns to operation S501.

In operation S505, the main controller 340 displays an UCA image obtained in the second mechanical index environment MI_2. In detail, the main controller 340 changes a mechanical index to be included in the second mechanical index environment in which the UCA nonlinearly moves and generates backscatter. According to the control of the main controller 340, the pulse controller 330 outputs a control signal to transmit an ultrasound signal in the second mechanical index environment, and the receiver 210 performs beamforming on an echo signal corresponding to ultrasound reflected by the object and then outputs. Also, the image processor 320 may obtain the UCA image based on the echo signal on which the beamforming is performed. The UCA image obtained as described above may be displayed through the display 60.

Here, methods of obtaining the tissue image and the UCA image may differ from each other. The tissue image may be generated based on a fundamental frequency of the echo signal, and the UCA image may be generated based on a frequency band wider than that of the tissue image. For example, the UCA image may be generated by extracting only harmonic frequency components from the echo signal. Hereinafter, pulse inversion imaging that is an example of a method of generating an UCA image will be described in detail.

Referring to FIGS. 8 to 10, in operation S511, the ultrasound imaging apparatus 1 transmits ultrasound of a first pulse corresponding to the second mechanical index to an object. In detail, the pulse controller 330 may output a control signal to generate a first pulse shown in FIG. 9.

In operation S512, the ultrasound imaging apparatus 1 receives a first echo signal reflected by the object. Here, the first echo signal reflected by the object includes a first tissue signal reflected by tissue and a first UCA signal reflected by an UCA. The first tissue signal is input while having the same phase as a fundamental frequency due to the linearity of the tissue, and the first UCA signal is input while being changed in phase due to a nonlinear movement of the UCA.

In operation S513, the ultrasound imaging apparatus 1 transmits an ultrasound signal of a second pulse having a phase opposite to that of the first pulse to the object. In detail, the pulse controller 330 may output a control signal to generate a second pulse shown in FIG. 9.

In operation S514, the ultrasound imaging apparatus 1 receives a second echo signal reflected by the object. The second echo signal reflected by the object includes a second tissue signal reflected by the tissue and a second UCA signal reflected by the UCA. Here, the second tissue signal is input while having the same phase as the fundamental frequency due to the linearity of the tissue, and the second UCA signal is input while being changed in phase due to the nonlinear movement of the UCA.

In operation S515, the ultrasound imaging apparatus 1 synthesizes the first echo signal with the second echo signal. When the first echo signal and the second echo signal generated by the pulses having opposite phases to each other are synthesized, the echo signal reflected by the tissue converges on 0 due to the linearity thereof as shown in FIG. 10, and only the echo signal reflected by the UCA is left. That is, when the echo signals of ultrasound having opposite phases are added, a fundamental frequency component is offset, and only harmonic frequency components are left.

In operation S516, the ultrasound imaging apparatus 1 generates an UCA image based on at least one harmonic signal. Here, the ultrasound imaging apparatus 1 may generate the UCA image using at least one of harmonic frequencies integer multiple times the fundamental frequency and a sub harmonic frequency, and may generate the UCA image using a plurality of different harmonic frequencies to improve the definition of the UCA image.

Hereinafter, a method of controlling the ultrasound imaging apparatus 1 according to an inflow of an UCA, according to another exemplary embodiment will be described with reference to FIG. 11.

Figure 11:
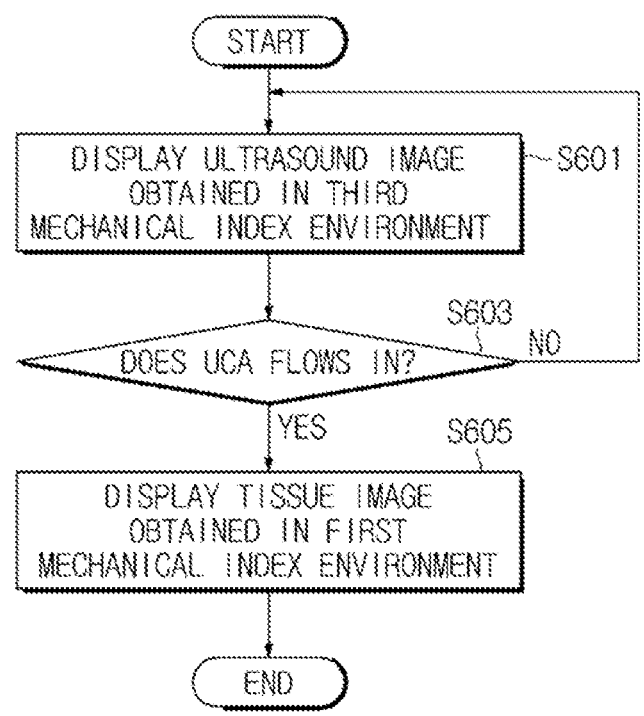
FIG. 11 is a flowchart illustrating a method of controlling an ultrasound imaging apparatus according to another exemplary embodiment.

FIG. 11 is a flowchart illustrating a method of controlling the ultrasound imaging apparatus 1, according to another exemplary embodiment. Although the ultrasound imaging apparatus 1 obtains an UCA image by lowering a mechanical index when an UCA flows therein in FIG. 7, the ultrasound imaging apparatus 1 may obtain a tissue image in a state in which the UCA flows therein by controlling the mechanical index to be lower than that of FIG. 7.

Referring to FIG. 11, in operation S601, the main controller 340 displays an ultrasound image obtained in the third mechanical index environment MI_3.

In operation S603, the UCA sensor 310 determines an inflow of an UCA or whether the UCA flows in the ultrasound image. When the UCA flows in (Yes for S603), the method continues in operation S605. Otherwise, the method returns to operation S601.

In operation S605, the main controller 340 displays a tissue image obtained in the first mechanical index environment MI_1. As described above, the UCA linearly moves in the first mechanical index environment MI_1. That is, in the first mechanical index environment MI_1, backscatter does not occur. Accordingly, when a mechanical index is set to be the first mechanical index environment MI_1, the tissue image may be obtained while minimizing an effect of the UCA.

Because the tissue image is obtained while controlling the mechanical index to be the first mechanical index environment MI_1 when the UCA is sensed as described above, a cavitation phenomenon caused by the collapse of the UCA may be prevented, and additionally the tissue image may be provided to the user even when the UCA is present in an ultrasound-scanned area. Although only one of the UCA image and the tissue image is obtained when the UCA flows therein in the exemplary embodiments, the ultrasound imaging apparatus 1 may obtain the UCA image and the tissue image, respectively, while changing the mechanical index. Hereinafter, another exemplary embodiment for providing an UCA image and a tissue image together will be described with reference to FIGS. 12 and 13.

Figure 12:
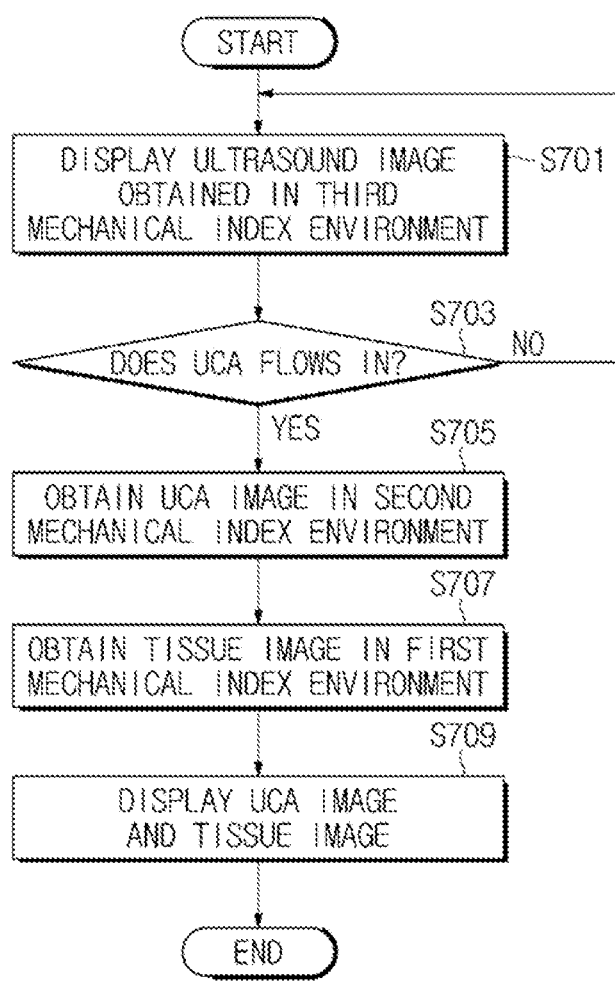
FIG. 12 is a flowchart illustrating a method of controlling an ultrasound imaging apparatus according to another exemplary embodiment.
Figure 13:
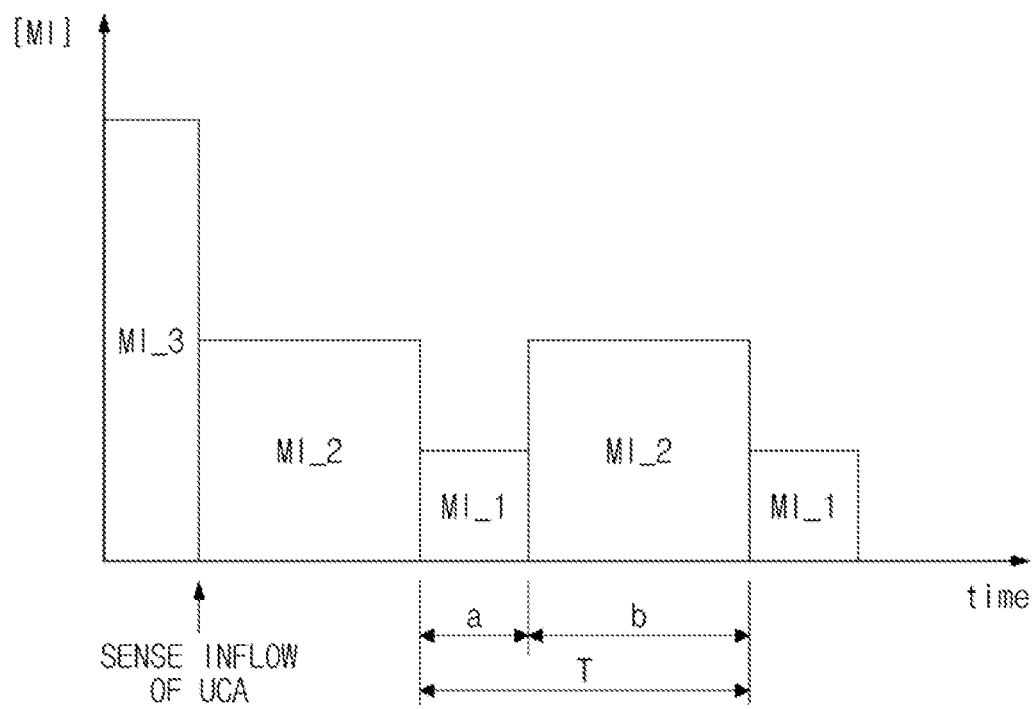
FIG. 13 is a graph illustrating a mechanical index environment change, according to an exemplary embodiment.

FIG. 12 is a flowchart illustrating a method of controlling the ultrasound imaging apparatus 1, according to another exemplary embodiment. FIG. 13 is a graph illustrating a mechanical index environment change, according another exemplary embodiment. Referring to FIGS. 12 and 13, in operation S701, the main controller 340 displays an ultrasound image obtained in the third mechanical index environment MI_3. Here, a range of the third mechanical index environment MI_3 may vary according to the setting of an ultrasound apparatus.

In operation S703, the UCA sensor 310 determines an inflow of an UCA or whether the UCA flows in the ultrasound image. When the UCA flows in (Yes for S703), the method continues in operation S705. Otherwise, the method returns to operation S701.

In operation S705, the main controller 340 obtains an UCA image in the second mechanical index environment MI_2 by lowering a mechanical index. For example, the UCA image may be obtained according to a pulse inversion imaging method.

In operation S707, the main controller 340 obtains a tissue image in the first mechanical index environment MI_1. As described above, due to a nonlinear movement of the UCA, it is difficult to obtain the UCA image and the tissue image at the same time. Accordingly, the tissue image may be separately obtained by controlling the mechanical index to be the first mechanical index environment MI_1 in which the UCA linearly moves.

In operation S709, the main controller 340 displays the UCA image and the tissue image. Here, the UCA image may be displayed on the first display 61, and the tissue image may be displayed on the second display 62.

Also, the main controller 340 may overlap the UCA image with the tissue image to be displayed on the first display 61 at the same time.

Meanwhile, obtaining the tissue image and the UCA image, as shown in FIG. 13, may be sequentially performed through time-sharing. For example, for each period T, the tissue image may be obtained in the first mechanical index environment MI_1 for a first time a, and the UCA image may be obtained in the second mechanical index environment MI_2 for a second time b. Because the tissue image and the UCA image are obtained periodically as described above, the tissue image and the UCA image may be provided together to the user.

Here, the period T may be a very short time. Although the second time b in the second mechanical index environment MI_2 is shown longer than the first time a in the first mechanical index environment MI_1, the first time a and the second time b may be the same, or the second time b may be longer than the first time a.

The UCA image and the tissue image are provided at the same time by changing the mechanical index environment as described above, thereby enhancing user convenience.

Meanwhile, the ultrasound imaging apparatus 1 may allow the UCA which flows therein to collapse, and may display a flow of an UCA that newly flows therein. Hereinafter, another exemplary embodiment for displaying the flow of the UCA will be described with reference to FIGS. 14 and 15.

Figure 14:
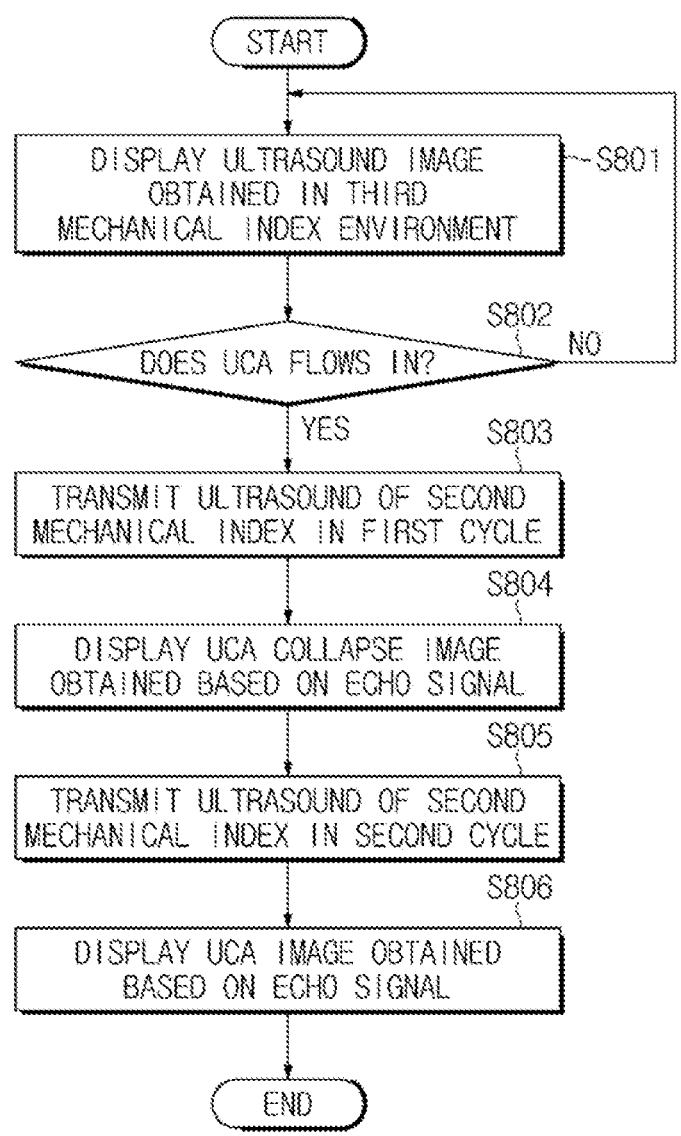
FIG. 14 is a flowchart illustrating a method of controlling an ultrasound imaging apparatus, according to another exemplary embodiment.
Figure 15:
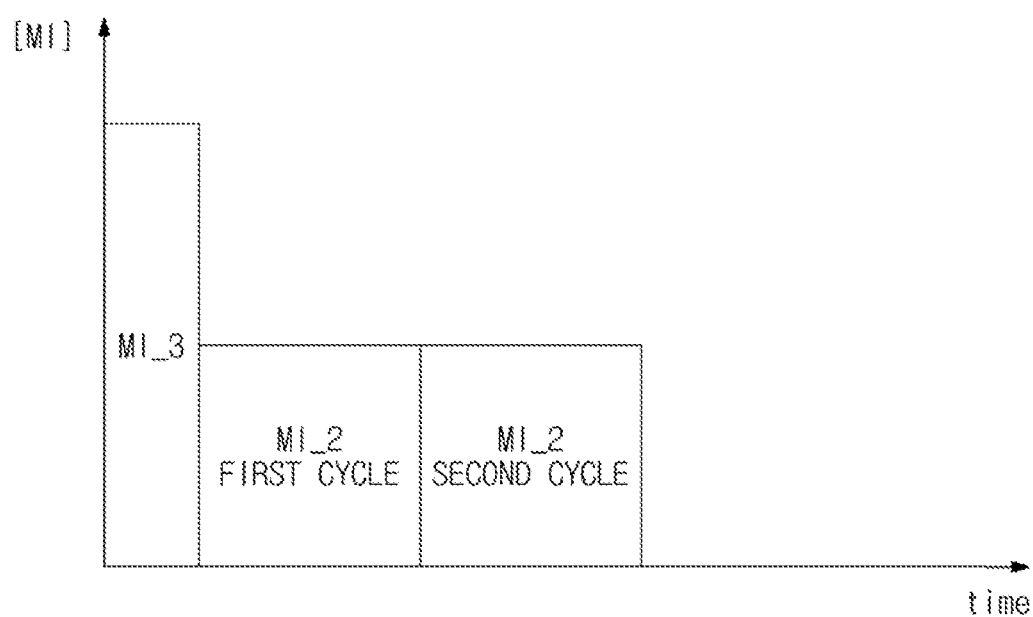
FIG. 15 is a graph illustrating a mechanical index environment change, according another exemplary embodiment.

FIG. 14 is a flowchart illustrating a method of controlling the ultrasound imaging apparatus 1, according to another exemplary embodiment. FIG. 15 is a graph illustrating a mechanical index environment change, according another exemplary embodiment.

Referring to FIGS. 14 and 15, in operation S801, the main controller 340 displays an ultrasound image obtained in the third mechanical index environment MI_3. Here, a range of the third mechanical index environment MI_3 may vary according to the setting of an ultrasound apparatus.

In operation S802, the UCA sensor 310 determines an inflow of an UCA or whether the UCA flows in the ultrasound image. When the UCA flows in (Yes for S802), the method continues in operation S803. Otherwise, the method returns to operation S801.

In operation S803, the main controller 340 transmits ultrasound in the second mechanical index environment MI_2 to an object in a first cycle. Here, the first cycle may have a relatively long pulse cycle to allow a large number of ultrasound signals to be transmitted per unit time.

As described above, the UCA does not collapse but nonlinearly moves in the second mechanical index environment MI_2. However, the object is continuously scanned with the ultrasound of the second mechanical index in the first cycle, and the UCA is scanned with a large amount of ultrasound per unit time, thereby allowing the UCA to collapse. That is, the ultrasound of the second mechanical index is continuously transmitted in the first cycle, which is relatively long, thereby allowing the UCA to collapse.

The UCA is allowed to collapse at a low mechanical index by controlling a pulse cycle as described above, thereby preventing the cavitation phenomenon caused by the rapid collapse of the UCA.

In operation S804, the ultrasound imaging apparatus 1 displays an UCA collapse image obtained based on at least one echo signal.

In operation S804, the ultrasound imaging apparatus 1 transmits ultrasound of the second mechanical index in a second cycle. Here, the second cycle is a pulse cycle that allows the UCA not to collapse but to nonlinearly move as described above.

In operation S806, the ultrasound imaging apparatus 1 displays an UCA image obtained based on at least one echo signal. Through the UCA image obtained as described above, the user may monitor the dispersion of the UCA. As described above, the UCA flows along a blood vessel of the object. Accordingly, because the UCA image obtained in the second cycle after all the UCA in an ultrasound-scanned area is allowed to collapse in the first cycle is similar to a bloodstream in the blood vessel, the user may diagnose the bloodstream using the UCA image obtained in the second cycle.

Meanwhile, the ultrasound imaging apparatus 1 may display a mechanical index environment together with the ultrasound image, thereby showing the set mechanical index environment to the user.

As is apparent from the above description, an ultrasound imaging apparatus that elastically controls a mechanical index and a method of controlling the same in accordance with exemplary embodiments are provided to provide an optimal ultrasound image to a user.

The foregoing exemplary embodiments and advantages are examples and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ultrasound imaging apparatus comprising:
   a probe;
   a memory configured to store a program; and
   a processor configured to execute the program to:
      control the probe to transmit an ultrasound signal of a third mechanical index to an object;
      determine whether an ultrasound contrast agent (UCA) flows in the object based on at least one of detecting a peak of a harmonic frequency signal included in an echo signal corresponding to the ultrasound signal of the third mechanical index allowing the UCA to collapse, detecting that the harmonic frequency signal changes by more than a threshold amount, and detecting that the harmonic frequency signal has a level greater than a threshold level;
      control the probe to transmit an ultrasound signal of a second mechanical index lower than the third mechanical index in a first cycle based on determining that the UCA flows in the object, the first cycle having a relatively long pulse cycle to allow the UCA to collapse;
      obtain a UCA collapse image based on an echo signal corresponding to the ultrasound signal of the second mechanical index;
      control the probe to transmit the ultrasound signal of the second mechanical index in a second cycle that allows the UCA to move nonlinearly; and
      obtain a UCA image based on an echo signal corresponding to the ultrasound signal of the second mechanical index allowing the UCA to move nonlinearly.

2. The ultrasound imaging apparatus of claim 1, wherein the processor is further configured to:
   control the probe to transmit an ultrasound si anal of a first mechanical index lower than the second mechanical index to the object, in response to determining that the UCA flows in the object;
   obtain a tissue image of the object using a fundamental frequency signal included in an echo si anal corresponding to the ultrasound signal of the first mechanical index allowing the UCA to move linearly;
obtain the UCA image, in a second mechanical index environment in which the ultrasound signal of the second mechanical index is transmitted, for a first time period; and
obtain the tissue image, in a first mechanical index environment in which the ultrasound signal of the first mechanical index is transmitted, for a second time period,
wherein the UCA image is generated in a first frequency band,
wherein the tissue image is generated in a second frequency band narrower than the first frequency band.

3. The ultrasound imaging apparatus of claim 2, further comprising a display configured to display the tissue image and the UCA image.

4. The ultrasound imaging apparatus of claim 3, wherein the display is further configured to alternately display the tissue image and the UCA image.

5. The ultrasound imaging apparatus of claim 3, wherein the display is further configured to display a mechanical index that is used by the ultrasound imaging apparatus.

6. The ultrasound imaging apparatus of claim 1, wherein the UCA image is generated by transmitting ultrasound signals according to a pulse inversion method.

7. A method of controlling an ultrasound imaging apparatus, the method comprising:
controlling a probe to transmit an ultrasound signal of a third mechanical index to an object;
determining whether an ultrasound contrast agent (UCA) flows in the object based on at least one of detecting a peak of a harmonic frequency signal included in an echo signal corresponding to the ultrasound signal of the third mechanical index allowing the UCA to collapse, detecting that the harmonic frequency signal changes by more than a threshold amount, and detecting that the harmonic frequency signal has a level greater than a threshold level;
controlling the probe to transmit an ultrasound si anal of a second mechanical index lower than the third mechanical index in a first cycle based on determining that the UCA flows in the object, the first cycle having a relatively long pulse cycle to allow the UCA to collapse;
obtaining a UCA collapse image based on an echo signal corresponding to the ultrasound signal of the second mechanical index;
controlling the probe to transmit the ultrasound signal of the second mechanical index in a second cycle that allows the UCA to move nonlinearity; and
obtaining a UCA based on an echo signal corresponding to the ultrasound signal of the second mechanical index allowing the UCA to move nonlinearly.

8. The method of claim 7, further comprising:
controlling the probe to transmit an ultrasound signal of a first mechanical index to the object, in response to determining that the UCA flows in the object;
obtaining a tissue image of the object using a fundamental frequency signal included in an echo signal corresponding to the ultrasound signal of the first mechanical index allowing the UCA to move linearly,
wherein the UCA image is generated in a first frequency band, and
wherein the tissue image is generated in a second frequency band narrower than the first frequency band.

* * * * *